(12) United States Patent
Okano et al.

(10) Patent No.: US 7,294,510 B2
(45) Date of Patent: Nov. 13, 2007

(54) PROCESS FOR PRODUCING NERVE STEM CELLS, MOTOR NEURONS, AND GABAERGIC NEURONS FROM EMBRYONIC STEM CELLS

(75) Inventors: Hideyuki Okano, Tokyo (JP); Takuya Shimazaki, Tokyo (JP)

(73) Assignee: Japan Science and Technology Corporation, Kawaguchi-shi (JP)

(*) Notice: Subject to any disclaimer, the term of this patent is extended or adjusted under 35 U.S.C. 154(b) by 573 days.

(21) Appl. No.: 10/472,490

(22) PCT Filed: Oct. 3, 2001

(86) PCT No.: PCT/JP01/08703

§ 371 (c)(1), (2), (4) Date: Sep. 30, 2003

(87) PCT Pub. No.: WO02/081663

PCT Pub. Date: Oct. 17, 2002

(65) Prior Publication Data

US 2004/0092012 A1    May 13, 2004

(30) Foreign Application Priority Data

Mar. 30, 2001    (JP) ............... 2001-099074

(51) Int. Cl.
*C12N 5/00* (2006.01)
*A61K 38/18* (2006.01)

(52) U.S. Cl. .............. 435/377; 435/325; 435/354; 435/365; 435/368; 530/399

(58) Field of Classification Search ............ None
See application file for complete search history.

(56) References Cited

U.S. PATENT DOCUMENTS

2003/0211605 A1* 11/2003 Lee et al. ............... 435/368

OTHER PUBLICATIONS

Finley et al. Journal of Neurobiol., Sep. 5, 1999, 40(3):271-87.*
K.S. O'Shea et al.: "Noggin induces a neural phenotype in ES cells, which is antagonized by EMP-4" Society for Neuroscience, vol. 24, Nos. 1-2, p. 1526 1998.
Sang-Hun Lee et al.: "Efficient generation of midbrain and hindbrain neurons from mouse embryonic stem cells" Nature Biotechnology, vol. 18, No. 6, pp. 675-677 Jun. 2000.
Tsutomu Nohno et al.: "Involvement of the sonic hedgehog genein chick feather formulation" Biotechnical and Biophysical Research Communications, vol. 206, No. 1, pp. 33-39 Jan. 5, 1995.
Streit, A., et al., "Chordin regulates primitive streak development and the stability of induced neural cells, but is not sufficient for neural induction in the chick embryo," Development 125, 507-519, 1998.

* cited by examiner

*Primary Examiner*—David S Romeo
*Assistant Examiner*—Daniel C Gamett
(74) *Attorney, Agent, or Firm*—Oblon, Spivak, McClelland, Maier & Neustadt, P.C.

(57) ABSTRACT

The present invention provides a method for producing motor neurons and GABAergic neurons characterized by including suspension-culturing embryonic stem cells in the presence or absence of a protein noggin to form embryoid bodies, selectively amplifying into neural stem cells from them by suspension culture in the presence of a fibroblast growth factor and a sonic hedgehog protein, and then differentiating the same. According to this method, at least motor neurons and GABAergic neurons can be systemically and efficiently produced from ES cells. Selective acquisition of neurons would be applicable to transplant therapy for amyotrophic lateral sclerosis, Huntington's chorea, Alzheimer's disease, etc.

8 Claims, 4 Drawing Sheets

PROCESS FOR PRODUCING NERVE STEM CELLS, MOTOR NEURONS, AND GABAERGIC NEURONS FROM EMBRYONIC STEM CELLS

TECHNICAL FIELD

The present invention relates to a method for selectively producing neural stem cells from embryonic stem cells (ES cells) and also to a method for selectively and efficiently producing motor neurons and GABAergic neurons.

BACKGROUND OF THE INVENTION

In the central nervous system of a mammal, neural stem cells exist through the entire life of the individual and contribute to the growth and homeostasis of the central nervous system by producing a variety of neurons and glia. Techniques that have recently been developed aiming at the isolation and culturing of neural stem cells from the brain of mammals, including humans, are expected to provide potential applications to the cell transplant therapies for various types of neurodegenerative diseases and injures. No appreciable achievement is still reported, however, despite some attempts exerted to obtain, from the neural stem cells cultured and amplified in vitro, different types of neurons that can be generated and differentiated from stem cells under control of diversified endogenous and exogenous factors, espeGially motor neurons that can be specifically generated at the initial stage of embryogenesis.

Accordingly, an object of the present invention is to provide means for efficiently inducing differentiation of ES cells, which have the capacity to differentiate into any type of mature cells in an individual, into neural stem cells maintaining properties of those cells in the early stage of development. Another object of the present invention is to provide a technique for selectively producing a specific type of neuron, such as motor neurons, from the neural stem cells.

DISCLOSURE OF THE INVENTION

The present inventors have investigated a variety of conditions under which it is necessary for embryoid bodies to be generated from ES cells, and for ES cells to differentiate and be induced into neural stem cells and eventually become the neurons. As a result, it has been found that the presence of noggin protein has a particularly important role in the induction of neural stem cells within embryoid bodies derived from ES cells; the use of a medium containing a fibloblast growth factor (FGF) and a sonic hedgehog protein is extremely efficient for amplifying neutral stem cells emerging in embryoid bodies; and when such neutral stem cells are differentiated, motor neurons and GABAergic neurons can be produced selectively and efficiently. Thus, the present invention has been accomplished on the basis of these findings.

Accordingly, the present invention provides a method for forming embryoid bodies, characterized by subjecting ES cells to suspension culture in the presence of noggin protein.

The present invention also provides a method for producing neural stem cells, characterized by subjecting ES cells to suspension culture in the presence or absence of noggin protein, to thereby form embryoid bodies, and subsequently subjecting the embryoid bodies to suspension culture in the presence of fibroblast growth factor and sonic hedgehog protein.

The present invention also provides a method for producing motor neurons and GABAergic neurons, characterized by subjecting ES cells to suspension culture in the presence or absence of noggin protein, to thereby form embryoid bodies, and subsequently subjecting the embryoid bodies to suspension culture in the presence of fibroblast growth factor and sonic hedgehog protein, to thereby induce neural stem cells, and differentiate the resultant neural stem cells.

BEST MODE FOR CARRYING OUT THE INVENTION

Figure 1:
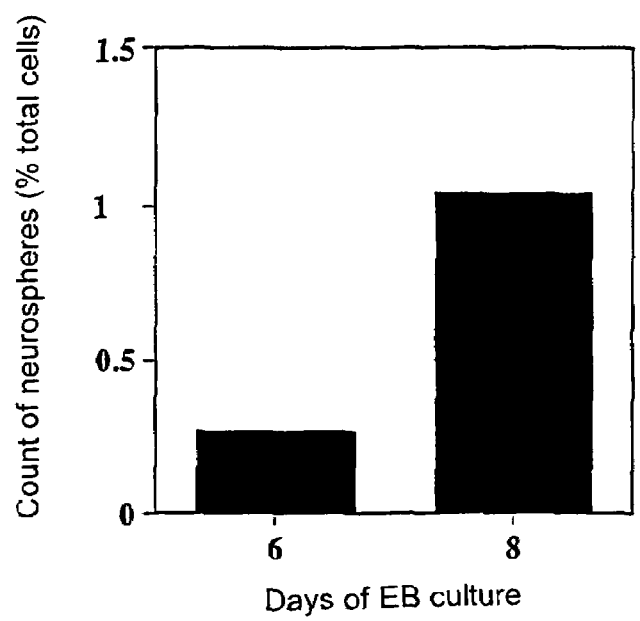
FIG. 1 shows the relation between days of culturing embryoid bodies and formation of neurospheres.

The ES cells used in the present invention may be those which-have already been established as cultured cells. For example, ES cell lines from mice, hamsters, pigs, and humans may be employed. Specific examples include 129/O1a-mouse-derived ES cells, such as EB3 and E14tg2. Preferably, the ES cells are subcultured in a GMEM medium or a similar medium supplemented with serum.

In the formation of embryoid bodies from ES cells, suspension culture of ES cells in a medium to which noggin protein has been added is effective for promoting differentiation-inducing efficiency from ES cells to neural stem cells. The noggin protein may be a Xenopus noggin protein. Alternatively, full-length cDNA of Xenopus noggin is transferred to COS7 cells, followed by culturing to cause transient expression of the noggin protein, and the resultant supernatant may be used as is. Preferably, the concentration of the noggin protein in medium is 1 to 50% (v/v) or thereabouts in terms of the volume of culture supernatant. Suspension culture of ES cells is performed by use of serum-containing $\alpha$-MEM medium for 4 to 8 days at a concentration of approximately $1 \times 10^5$ ES cells/mL. Examples of useful sera include bovine serum and pig serum. The serum concentration is 5 to 15%, preferably 8 to 12%. Preferably, 2-mercaptoethanol is added to the $\alpha$-MEM medium in such an amount that achieves a concentration of 0.01 to 0.5 mM, particularly 0.05 to 0.2 mM. The culturing is preferably performed in 5% $CO_2$, at 35-40° C.

It is highly preferred that the noggin protein be added during formation of embryoid bodies; i.e., during the period from day 0 to day 6 of culturing.

In order to amplify neural stem cells which have been obtained from ES cells via the above-prepared embryoid bodies, suspension culture is performed by use of a neural stem cell amplification medium containing not only a fibroblast growth factor but also a sonic hedgehog protein. The addition of sonic hedgehog protein promotes efficiency of inducing differentiation of neural stem cells to motor neuron precursors, and also improves multiplication efficiency of the neural stem cells. Moreover, through subsequent differentiation culturing, the neural stem cells are in fact differentiated into motor neurons and GABAergic neurons.

A preferred fibroblast growth factor (FGF) is FGF-2. The FGF content of the medium is preferably 5 to 50 ng/mL, more preferably 10 to 40 ng/mL. Examples of preferred sonic hedgehog proteins include mouse sonic hedgehog protein. The sonic hedgehog protein content of the medium is 1 to 20 nM, preferably 1 to 10 nM.

The medium is preferably a DMEM medium containing, in addition to the aforementioned components, glucose, glutamine, insulin, transferrin, progesterone, putrecine, selenium chloride, heparin, etc. Use of a DMEM:F12 medium is particularly preferred. The culturing is preferably performed in 5% $CO_2$, at 35-40° C., for a period of 7 to 9 days.

Through the above-described suspension culture, single-cell-derived, aggregated masses of cells, called neurospheres, are formed.

The thus-obtained neurospheres have originated solely from neural stem cells, and thus the above-mentioned culture method is proven to attain very high differentiation efficiency.

When the thus-obtained neural stem cells are cultured in an ordinary differentiation medium, differentiation into only motor neurons and GABAergic neurons alone is induced. Here, a preferred differentiation-inducing medium is a DMEM:F12 medium containing glucose, glutamine, insulin, transferrin, progesterone, putrecine, and selenium chloride (in other words, a medium designed for amplifying neural stem cells but excluding FGF and heparin). In this medium, sonic hedgehog protein may or may not be present. The culturing is preferably performed in 5% $CO_2$, at 35-40° C., for 5 to 7 days.

Neural cells obtained from ES cells through conventional techniques of differentiation contain not only neurons but also significant amounts of glia cells, among other cells. Thus, heretofore, they have only limited usage value. In contrast, wherein the neurons obtained by working the present invention are substantially formed only of motor neurons and GABAergic neurons.

EXAMPLES

The present invention will next be described by way of examples, which should not be construed as limiting the invention thereto.

A. Materials and methods (1) Culture-Passage of Mouse ES Cells and Formation of Embryoid Bodies E14tg2a ES cells derived from 129/O1a mice and EB3 ES cells (which allow selection of undifferentiated ES cells through insertion of blasticidin-resistant gene to the Oct3/4 locus of E14tg2a) were subcultured by a routine method in a GMEM medium (Glasgow minimum essential medium) containing 10% fetal calf serum, nonessential amino acids, 1 mM sodium pyruvate, 0.1 mM 2-mercaptoethanol, and 1,000 U/mL leukemia inhibitory factor (LIF). The culture conditions were 5% $CO_2$ at 37° C. (hereafter, when "culture" is referred to, these conditions apply).

Formation of embryoid bodies (EBs) from the ES cells was carried out as follows. Firstly, ES cells were washed with PBS. Subsequently, the washed cells were treated with 0.25% trypsin—1 mM EDTA, and then the treatment reaction was stopped. The cells were dissociated by pipetting, and seeded in a bacterial culture dish filled with α-MEM medium containing 10% fetal calf serum and 0.1 mM 2-mercaptoethanol. In the presence or absence of noggin protein, suspension culture was performed for 4 to 8 days, whereby EBs were formed. The noggin protein employed was a culture supernatant of COS7 cells to which full-length cDNA of Xenopus noggin had been introduced for transitory expression.

(2) Isolation of Neural Stem Cells by Selective Culture of EBs

The EBs formed as described above, together with the culture liquid, were transferred to a centrifuge tube. The tube was allowed to stand for 10 minutes, so that the EBs were sedimented at the bottom. The supernatant was removed, and the EBs were re-suspended in PBS. The test tube was allowed to stand for 10 minutes again. The supernatant was removed, and the EBs were re-suspended in a solution containing 0.25% trypsin and 1 mM EDTA PBS, followed by incubation at 37° C. for five minutes. The protein degradation reaction was stopped by use of α-MEM medium containing 10% fetal calf serum. The cells were dissociated by pipetting. The dissociated cells were centrifugally washed with α-MEM medium twice, and seeded at a concentration of $5 \times 10^4$ cells/mL in either of the following mediums designed for neural stem cell amplification: a 1:1 medium of DMEM (Dulbecco's modified Eagle's medium) and F12, where the DMEM had been supplemented with glucose (0.6%), glutamine (2 mM), insulin (25 μg/mL), transferrin (100 μg/mL), progesterone (20 nM), putrecine (60 μM), selenium chloride (30 nM), FGF-2 (20 ng/mL), and heparin (2 μg/mL); or the same medium but further containing a mouse sonic hedgehog (5 nM), followed by suspension culture for 7 to 9 days, whereby neurospheres (cell clusters derived from a single cell) were formed. The neurospheres were centrifugally washed with a differentiation medium containing neither FGF-2 nor heparin, and the washed cells—in the "as washed" state or after dissociated through pipetting—were seeded in a culture petri dish coated with poly-L-ornithine and filled with a differentiation medium, whereby differentiation is allowed to proceed in the presence or absence of a sonic hedgehog protein (5 nM) for 5 to 7 days. Separately, the above-obtained neurospheres were again dissociated into single cells, subcultured in a medium designed for amplification of neural stem cells, to thereby form secondary neurospheres. The thus-obtained secondary neurospheres are also caused to differentiate as described above.

(3) Identification of Differentiated Neurons and Glia Cells Through Immunostaining The thus-differentiated neurons and glia cells were identified by a routine immunostaining method using a fluorescent antibody. Motor neurons were identified by mouse anti-Isl-1 monoclonal antibody, goat anti-ChAT polyclonal antibody, and mouse anti-β-III tublin monoclonal antibody; and GABAergic neurons were identified by rabbit anti-GAD67 polyclonal antibody. Regarding glia cells, astrocytes were identified by rabbit anti-GFAP polyclonal antibody, and oligodendrocytes were identified by mouse anti-04 monoclonal antibody.

B. Test results (1) Isolation and Purification of Neural Stem Cells by Selective Culture of EBs Firstly, the inventors focused on the initial stage of differentiation of ES cells via formation of EBs, and investigated as to when neural stem cells emerged during culture. Specifically, EBs which had undergone 4 to 8 days of culture were dissociated into single cells, followed by culture for 7 days in a medium designed for amplifying neural stem cells, whereby neurospheres were formed. The neurospheres were transferred to a differentiation medium, and allowed to differentiate. Thereafter, their differentiation capacity was checked. Also, neurospheres were subcultured for checking their self-renewal capacity.

FIG. 1 shows the results of selective culture of neural stem cells (the neurosphere method), wherein 6 or 8 days after start of EB formation through suspension culture, the formed EBs were dissociated into single cells and subjected to the neurosphere method. The number of the neural stem cells emerged in the EBs was taken as that of the obtained neurospheres. Neural stem cells (capable of forming neurospheres) which were to be identified by the present method were virtually not detected until day 4 of culture. On day 6 of culture, neural stem cells accounted 0.25% of all the cells, and on day 8, neural stem cells accounted 1.1%, thus gradual increase in cell count was acknowledged.

Figure 2:
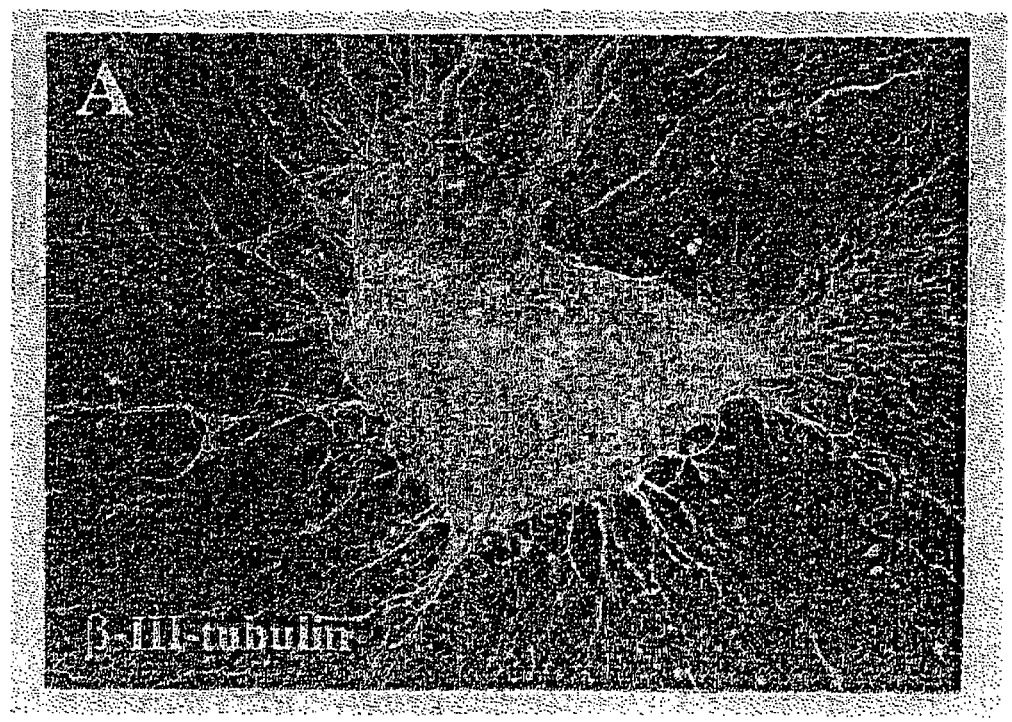
FIG. 2 shows an image of immunostaining of neurospheres after differentiation. The stained region shows expression of $\beta$-III-tubulin, which indicates a neuron.
Figure 3:
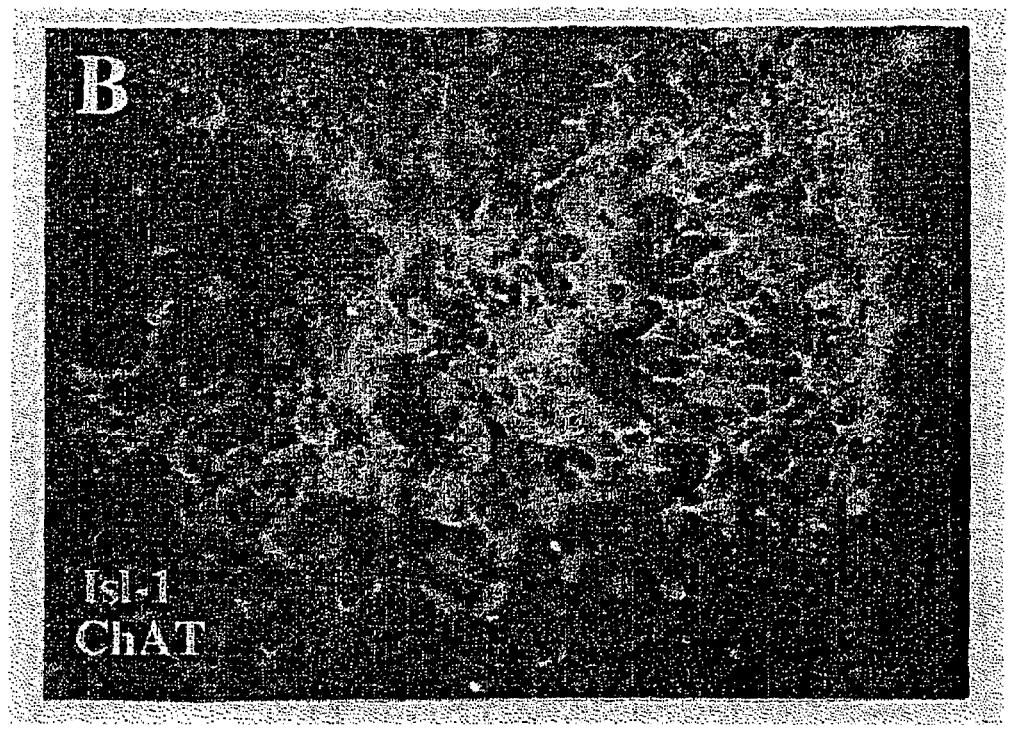
FIG. 3 shows another image of immunostaining of differentiated neurospheres by anti-1st-1 and anti-ChAT (choline acetyltransferase) antibodies which are markers for motor neurons.
Figure 4:
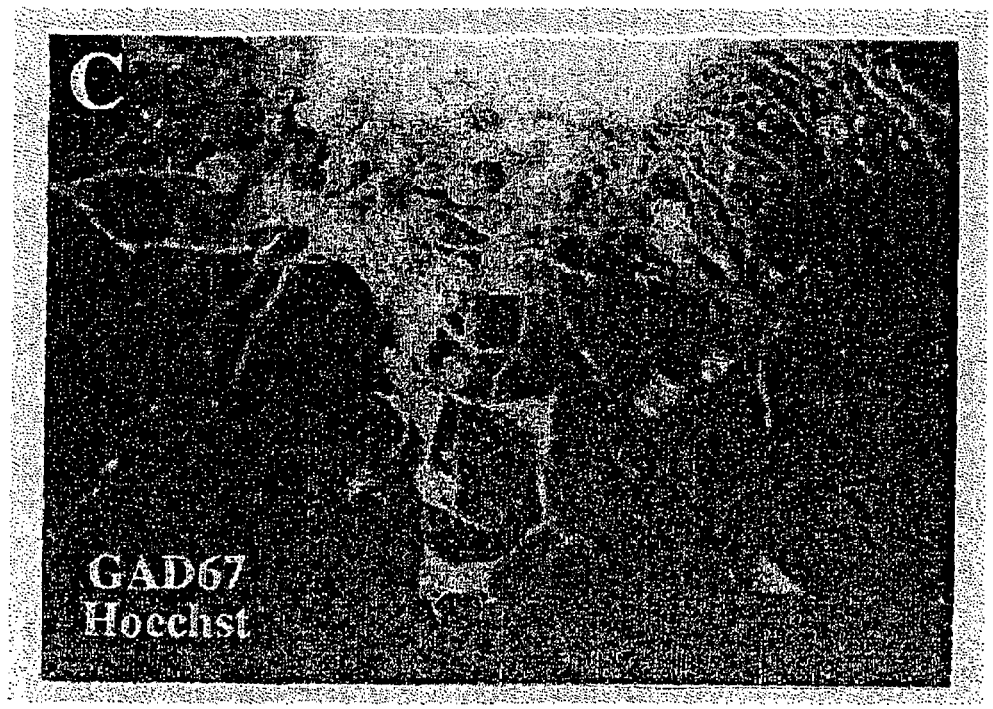
FIG. 4 shows yet another image of immunostaining of differentiated neurospheres by anti-GAD (glutamic acid decarboxylase) 67 antibody.

The neurospheres obtained from the EBs on day 6 (see FIG. 1) were cultured for 7 days under differentiation conditions, and their differentiation capacity was checked through immunostaining. The results are shown in FIGS. 2 to 4. When triple immunostaining was performed by use of β-III-tubulin (a marker for neurons) and GFAP and anti-04 antibody (markers for glial cells), virtually all neurospheres were found to be formed only of neurons, which express β-III-tubulin, and no glial cells were detected (FIG. 2). The neurons were found to contain at least motor neurons expressing at least Isl-1 and ChAT (note: the motor neurons are seen in FIG. 3 as round images and fibrous images) and GABAergic neurons expressing GAD67 (note: the GABAergic neurons are seen in FIG. 4 as fibrous images).

Figure 5:
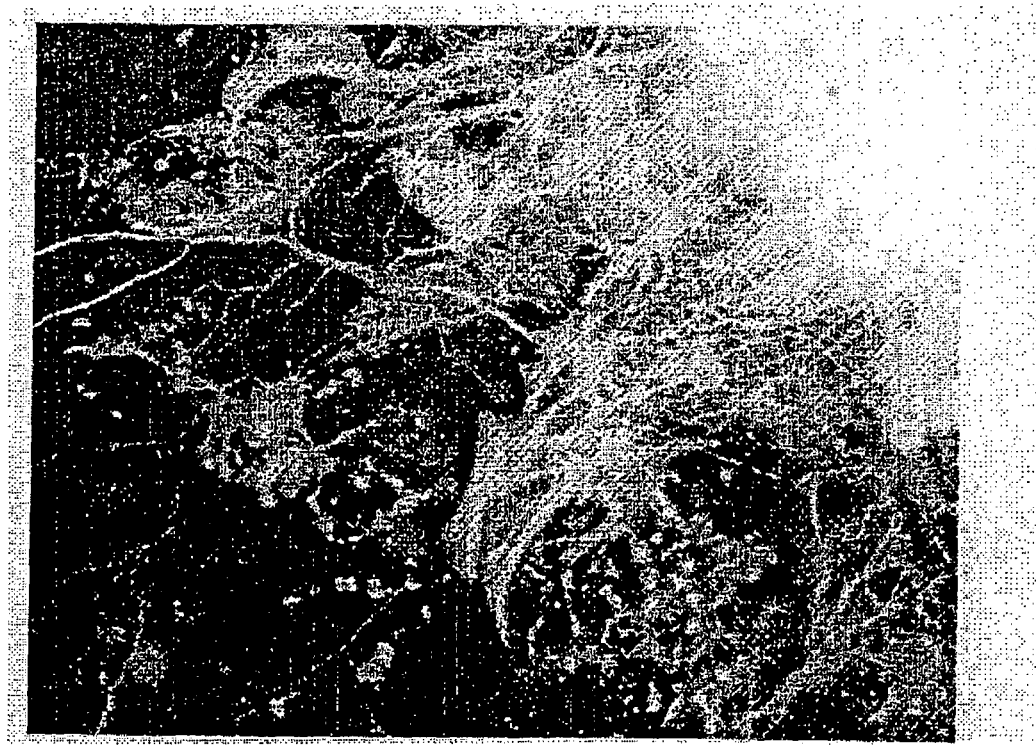
FIG. 5 shows an image of immunostaining of differentiated neurospheres that have undergone subculture. Cells were immunolabeled by anti-$\beta$-III, GFAP, and 04 antibodies.
Figure 6:
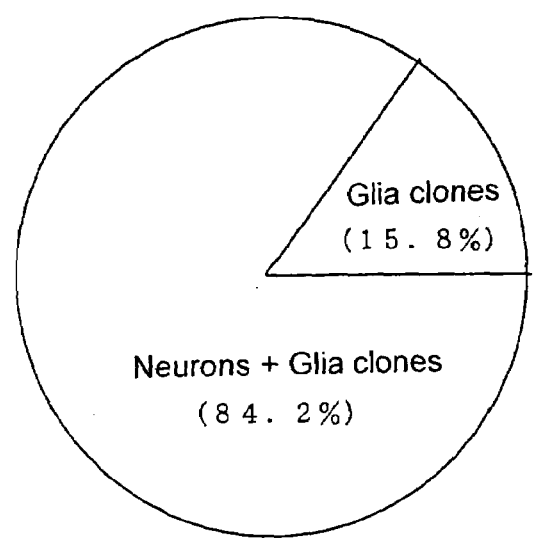
FIG. 6 shows the percentage of neurons and glia cells after subculture of neurospheres.

Moreover, the obtained neurospheres were subjected to subculture, to thereby obtain secondary neurospheres. The secondary neurospheres were cultured for 7 days under differentiation conditions, and their differentiation capacity was checked through immunostaining. As a result, all the neurospheres were found to contain glia cells (FIG. 5); with 84.2% thereof containing both neurons and glias (FIG. 6). FIG. 5 shows the results of triple immunostaining with β-III-tubulin (definite thin fibers), GFAP (portions surrounding those of β-III-tubulin), and anti-04 antibody (portions surrounding those of GFAP).

As a result, the following was confirmed: When neurospheres are dissociated into single cells and then subcultured to thereby cause formation of new neurospheres and differentiation, most clones thereof contain both neurons and glias, and like the case in which glia cells emerge in a later period in development of actual central nervous system, neural stem cells isolated from EBs, after undergoing subculture, also exhibit pluripotent capacity.

Figure 7:
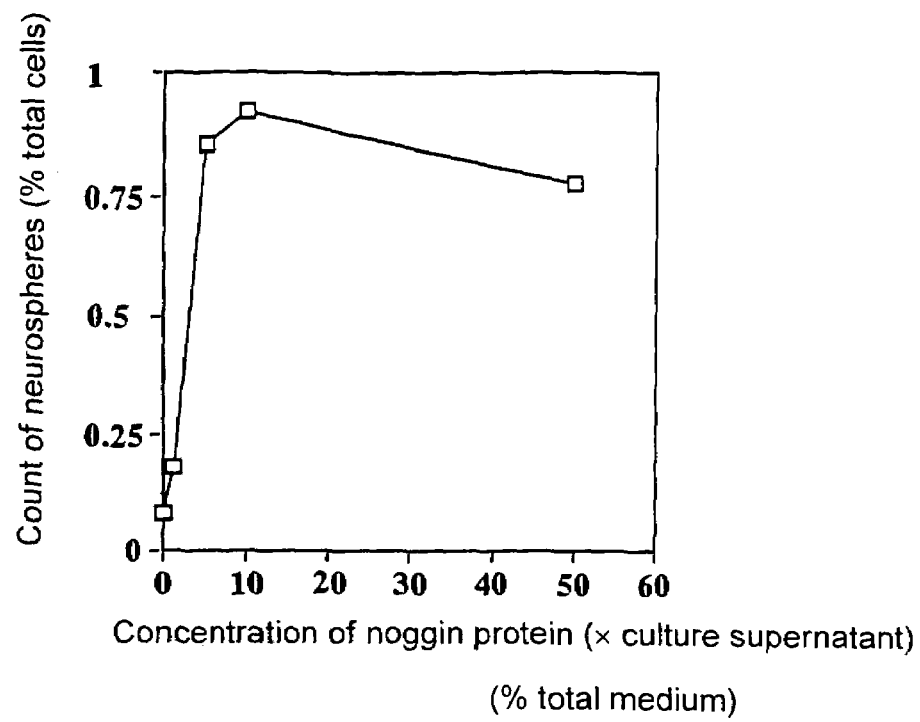
FIG. 7 shows the effect of addition of a noggin protein.

(2) Improvement of Efficiency in Inducing Neural Stem Cell Differentiation by Use of Noggin Protein In an attempt to improve efficiency in inducing neural stem cell differentiation, during EB formation (6 days), noggin protein was added. The noggin protein employed was in the form of solution prepared by use of the supernatant of the culture in which full-length cDNA of Xenopus was inserted into a pEF-BOS expression vector and then transfected into COS7 cells for transient expression. The control employed was a supernatant of culture of COS7 cells to which only the expression vector had been incorporated. As shown in FIG. 7, the number of neurospheres formed of neural stem cells and induced to differentiate among EBs increases with the volume of the noggin culture supernatant, reaching a peak at 1/10 in volume.

Figure 8:
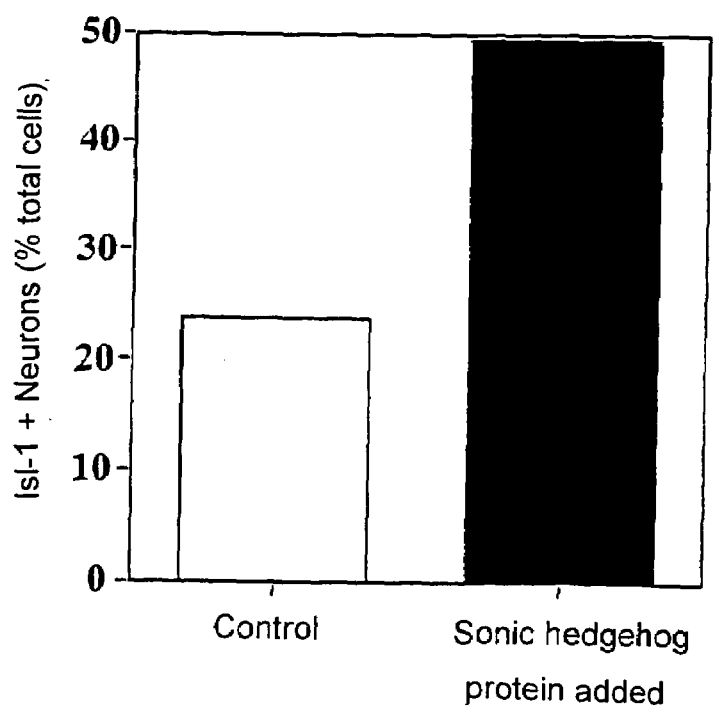
FIG. 8 shows the effect of addition of a sonic hedgehog protein.

(3) Improvement in Efficiency of Motor Neuron Differentiation by Use of Sonic Hedgehog Protein In an attempt to improve efficiency of motor neuron production and differentiation from EB-derived neural stem cells, sonic hedgehog protein was added to proliferating neural stem cells, in other words, during formation of primary culture neurospheres derived from EBs, and the effect of the addition was studied. After the neurospheres were dissociated into single cells and cultured for 5 days in a differentiation medium, motor neurons were identified through double immunostaining by use of Isl-1 and β-III-tublin, and the number thereof was quantified. As shown in FIG. 8, production of motor neurons doubled as a result of addition of 5 nM sonic hedgehog protein. When sonic hedgehog protein was added to the differentiation medium in which neural differentiation took place, no effect of addition was observed.

INDUSTRIAL APPLICABILITY

The present invention has thus found that ES cells have capability of producing at least motor neurons and GABAergic neurons systematically and efficiently. It also suggests that if neurons are selectively obtained therefrom, ES cells might make it possible to bring the potential use to transplant therapies for amyotrophic lateral sclerosis, Huntinton's chorea, Alzheimer's disease, etc.

The invention claimed is:

1. A method for forming embryoid bodies, which comprises subjecting embryonic stem cells to suspension culture in the presence of a noggin protein, wherein said noggin protein is added to the culture prior to formation of embryoid bodies.

2. A method for producing neural stem cells, which comprises subjecting embryonic stem cells to suspension culture in the presence of a noggin protein, to thereby form embryoid bodies, and subsequently subjecting the embryoid bodies to suspension culture in the presence of a fibroblast growth factor and a sonic hedgehog protein to thereby form a culture of neural stem cells.

3. The method according to claim 2, wherein concentration of the fibroblast growth factor in culture medium is 5 to 50 ng/mL, and that of the sonic hedgehog protein in culture medium is 1 to 20 nM.

4. A method for producing motor neurons and GABAergic neurons, which comprises subjecting ES cells to suspension culture in the presence of a noggin protein, to thereby form embryoid bodies, and subsequently subjecting the embryoid bodies to suspension culture in the presence of a fibroblast growth factor and a sonic hedgehog protein, to thereby induce formation of neural stem cells, and differentiating the resultant neural stem cells in a differentiation medium.

5. The method according to claim 4, wherein concentration of the fibroblast growth factor in culture medium is 5 to 50 ng/mL, and that of the sonic hedgehog protein in culture medium is 1 to 20 nM.

6. The method according to claim 4, wherein the resultant neurons are substantially formed of motor neurons and GABAergic neurons.

7. The method according to claim 5, wherein the resultant neurons are substantially formed of motor neurons and GABAergic neurons.

8. The method according to claim 2, wherein the culture of neural stem cells comprises neurospheres.

* * * * *